United States Patent [19]

Krbechek

[11] 4,201,716

[45] May 6, 1980

[54] PREPARATION OF 22-STEROID ACETALS

[75] Inventor: Leroy O. Krbechek, Golden Valley, Minn.

[73] Assignee: Henkel Corporation, Minneapolis, Minn.

[21] Appl. No.: 890,102

[22] Filed: Mar. 27, 1978

[51] Int. Cl.² .............................. C07J 7/00; C07J 9/00
[52] U.S. Cl. ................................ 260/397.4; 260/397.3
[58] Field of Search .............. 260/397.3, 397.4, 397.47

[56] References Cited

U.S. PATENT DOCUMENTS

| | | | |
|---|---|---|---|
| 2,701,806 | 2/1955 | Donia | 260/397.3 |
| 3,255,218 | 6/1966 | Herzog | 260/397.45 |

FOREIGN PATENT DOCUMENTS 539441  10/1940  United Kingdom .................. 260/397.3

*Primary Examiner*—Ethel G. Love
*Attorney, Agent, or Firm*—Forrest L. Collins

[57] ABSTRACT

The present invention relates to the preparation and recovery of $C_{21}$ steroid acetals. The present invention also discusses the recovery of a 20 steroid carboxaldehyde from a mixture containing a 3,20 dione steroid.

25 Claims, No Drawings

PREPARATION OF 22-STEROID ACETALS

BACKGROUND OF THE INVENTION

1. Field of the Invention

This invention discusses useful techniques in the production and recovery of steroids.

2. Description of the Art Practices

The production of progesterone from the corresponding aldehyde via the intermediate step of conversion by acetic anhydride is known. This process is discussed in an article entitled "Progesterone from 3-Acetoxybisnor-5-cholenaldehyde and 3-Ketobisnor-4-cholenaldehyde" by Heyl et al, Volume 72, pp 2617-2619, June, 1950.

In the Heyl et al reference the 3-ketobisnor-4-chlorenaldehyde is converted via acetic anhydride using sodium acetate as a catalyst into the corresponding bisenol and enol acetate. The bisenol acetate and enol acetate are described in the reference as being conveniently ozonized directly to progesterone.

The Heyl et al reference further states that 3-beta-acetoxybisnor-5-cholenaldehyde may also be converted via an ozonolysis step to progesterone. In either reaction the 3-ketobisnor-4-cholenaldehyde which is a 20 steroid carboxaldehyde, will not be fully converted to progesterone. The presence of the unconverted aldehyde in the mixture with progesterone is, of course, undesirable noting that the progesterone is used for human pharmaceutical purposes.

Thus, given the fact that a convenient route for progesterone production exists from a particular 20 steroid carboxaldehyde, it is desirable that such reaction be conducted as efficiently as possible. Of course, as stated above, it is also extremely desirable to minimize the amount of aldehyde which remains in mixture with the progesterone.

It has also been suggested by Herr et al in "Enamine" Derivatives of Steroidal Carbonyl Compounds, JACS; Volume 74, July 20, 1952, pp 3627-3630 that the 3-keto-bisnor-4-cholenaldehyde could be converted by a secondary amine such as piperidine through dehydration in the presence of potassium carbonate to give a dipiperidyl compound. Partial degradation of the dipiperidyl compound regenerates piperidine and a compound designated as an "enamine" which is an alpha, beta unsaturated amine of the particular steroid. Through subsequent steps the "enamine" could be converted by ozonolysis to give progesterone. In following the teachings of this reference, as well as the earlier JACS article, it is noted that some unreacted steroid carboxaldehyde will invariably be present in the final mixture containing the progesterone. For the reasons given above, this steroid aldehyde in the final product is undesirable and should be minimized.

Therefore, when the production of progesterone is attempted through either route, it is desirable in view of economy and purity of the end product that the steriod carboxaldehyde be removed from a mixture of that material and the progesterone.

In the present invention, the separation of such steroid carboxaldehydes from progesterone is accomplished and the steroid carboxaldehyde is recovered. The separation is accomplished by converting the steroid carboxaldehyde to the corresponding acetal followed by solvent extraction of the components. The steroid carboxaldehyde is then recycled into the feed material for the progesterone production. While some hemiacetal steroids are known from U.S. Pat. No. 3,264,285 to Borrevang issued Aug. 2, 1966 it is not suggested that acetal formation can be used to increase progesterone production.

Throughout the specification and claims, percentages and ratios are by weight and temperatures are in degrees Celsius, unless otherwise indicated. Numerals preceding the term steroid indicate the position of the named functional group on the steroid.

SUMMARY OF THE INVENTION

The present invention describes a process for separating a 20 steroid carboxaldehyde from a reaction mixture containing a 3,20 dione steroid and the 20 steroid carboxaldehyde by the transformation of the aldehyde to the corresponding acetal followed by solvent extraction of the acetal and the dione steroid into separate fractions.

The present invention also describes as novel compounds the 22-acetals of the corresponding 20 steroid carboxaldehydes.

DETAILED DESCRIPTION OF THE INVENTION

In the primary aspect of the present invention the 20 steroid carboxaldehyde (I) is 3-ketobisnor-4-cholenaldehyde (also referred to as 3-keto-4-pregnene-20-carboxaldehyde) as shown in II below. The 3,20 dione steroid (III) most often encountered in the present invention is progesterone as shown in IV. As previously indicated, the present invention relates to the separation of the 20 steroid carboxaldehyde from any reaction mixture containing the corresponding 3,20 dione steroid. The invention has wide application in that it is the aldehyde and keto groups which account for the solubility difference during extraction. In other words the basic ring structure may be widely modified as long as the 3-keto and the 20 carboxaldehyde (or keto) structure, as the case may be, is left intact. The presence of unsaturation in the steroid ring structure or the presence of substitients does not substantially affect the extractibility of the steroid carboxaldehyde and the dione steroid. However, in most cases the practical application of the present invention will be the separation of 3-ketobisnor-4-cholenaldehyde from progesterone.

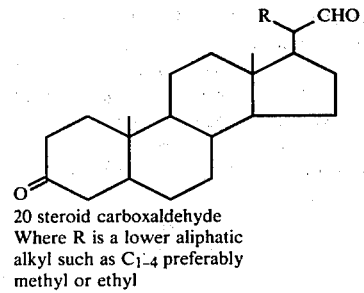

20 steroid carboxaldehyde
Where R is a lower aliphatic
alkyl such as $C_{1-4}$ preferably
methyl or ethyl

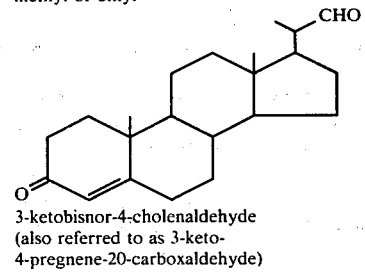

3-ketobisnor-4-cholenaldehyde
(also referred to as 3-keto-
4-pregnene-20-carboxaldehyde)

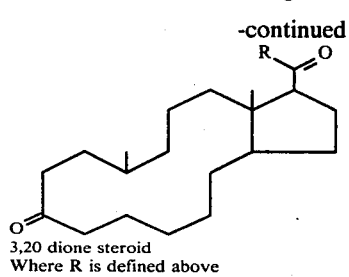

3,20 dione steroid
Where R is defined above

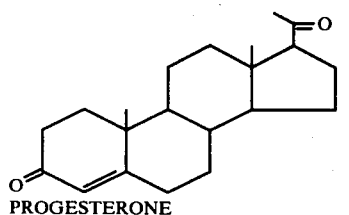

PROGESTERONE

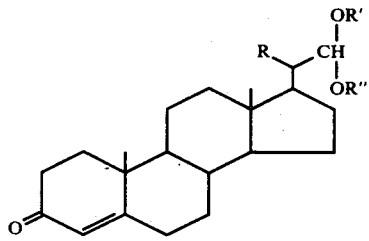

A 3-keto-steroid-21-acetal
Where R is defined above.
Where R is methyl and R' and R" are butyl the compound becomes 3-keto-20-methyl-4-pregnene-21-butylacetal.

The mixture of the 20 steroid carboxaldehyde and the 3,20 dione steroid may effectively be present in any proportion. That is, the 20 steroid carboxaldehyde will in most cases be present in a fairly substantial quantity from the processing of either the Heyl or Herr references discussed supra and herein incorporated by reference. Therefore, while the present invention is fully capable of minimizing the 20 steroid carboxaldehyde content present in a mixture containing that material and a 3,20 dione steroid, the practical applications of the present invention will be where the steroid carboxaldehyde is present in the mixture with the 3,20 dione steroid at a weight ratio of from about 5:1 to about 1:20, preferably from about 3:1 to about 1:10.

The next aspect of the present invention is that of the acetal formation. As shown in V above, the acetal structure contains substituants designated R' and R". R' and R" may be the same or different aliphatic radicals. For the sake of simplicity, the structure R'O or R"O is referred to as an alkoxy moeity. In the most convenient aspect of the present invention R'O and R"O are the same and may correspond to a lower alcohol having from one to four carbon atoms. Preferably R'O and R"O are selected from the group consisting of 1-butanol, 2-butanol, isobutyl alcohol, 1-propanol, and 2-propanol or mixtures thereof. In the most preferred aspect of the present invention R'O and R"O are both derived from 2-butanol.

At this point it should also be mentioned that in one aspect of the present invention, the process for conducting the acetal formation from the 20 steroid carboxaldehyde is that of carrying out the reaction in a solvent which is identical to the alcohol corresponding to R'O and R"O. Thus where the dibutal acetal (preferably di-normal-butyl acetal) of 3-keto-4-pregnene-20-carbox-aldehyde is to be formed, the solvent should be 1-butanol. As the solvent is a reactant during acetal formation, any suitable amount of the alcohol may be used. Conveniently, the ratio of the alcohol used to form the acetal of the 20 steroid carboxaldehyde is from about 100:1 to about 1:1 on an equivalent basis. Alternatively the acetal formation may be conducted using the extraction solvent as discussed below as a medium for the reaction while employing sufficient alcohol to allow acetal formation.

Another useful ingredient in forming the acetal is a desicant to scavange the water which is liberated. Any scavenger which does not interfere with acetal formation may be used. Such materials include triethylorthoformate. The desicant should be employed at equivalent amounts to the hemiacetal of the 20 steroid carboxaldehyde. That is, the corresponding hemiacetal will be an intermediate product in forming the acetal and the equivalent use of the desicant is necessary to achieve complete conversion of the hemiacetal to the acetal.

As the corresponding hemiketal and ketal of the 3,20 dione steroid may be formed at either the 3 or 20 keto position, excessive use of the desicant or the later discussed acetal catalyst should be avoided. The hemiketal and ketal of the 3,20 dione steroid have sufficiently similar characteristics to the acetal of the 20 steroid carboxaldehyde to make solvent extraction nearly impossible. With respect to the desicant, the amount employed is preferably less than 2.5 equivalents, and preferably less than 1.5 equivalents per equivalent of the 20 steroid carboxaldehyde.

The acetal formation is preferably assisted by utilizing acetal promoting catalysts. Such materials include the use of catalytic amounts of strong Lewis acids such as p-toluenesulfonic acid, anhydrous hydrochloric acid, trifluoroacetic acid, trichloroacetic acid, oxalic acid and mixtures thereof. The preferred pH for the reaction mixture in the acetal conversion process is therefore slightly acidic due to the fact that acetal formation does not readily take place at neutral or alkaline conditions. The corresponding hemiacetal formation will take place under acid, basic or neutral reaction conditions. However, it is desirable that the acetal formation be as complete as possible as it has been found that the hemiacetal of the 20 steroid carboxaldehyde is considerably more difficult to separate from the 3,20 dione steroid. That is, the hemiacetal is unstable and can regenerate the 20 steroid carboxaldehyde, thus rendering solvent extraction of limited value. Thus, for the reasons given above, the pH of the reaction mixture is conveniently maintained below about 7, preferably from about 1 to about 6. Any suitable acid material which will not interfere in the acetal formation may be utilized to adjust the pH as indicated. It should be noted in the preferred aspect of the present invention, that small amounts of p-toluenesulfonic acid will function sufficiently to place the pH of the reaction mixture in the acid range.

In the preferred aspect of the present invention a trace amount of p-toluenesulfonic acid and triethylorthoformate utilized on an equivalent basis to the hemiacetal of the 20 steroid carboxaldehyde are employed.

The conversion of the 20 steroid carboxaldehyde to the corresponding acetal in the reaction mixture containing the 3,20 dione steroid is conveniently conducted at a temperature range at from about 5 degrees C. to about 75 degrees C., preferably from about 10 degrees C. to about 40 degrees C. The formation of the acetal is facilitated by moderate stirring for a period of slightly more than one hour. In most cases, the acetal formation will be complete in a period of from about 1 to 3 hours. When less time is allowed for acetal conversion, greater amounts of catalyst must be used or the conversion will not be complete in the desired time. Preferably, longer acetal reaction time using minimum amounts of the acetal catalyst are preferred to avoid ketal or hemiketal conversion. Thus, sufficient reaction time must be allowed in order to complete the conversion to the acetal. If desired, the reaction mixture can be sampled to determine the amount of acetal formation and thus for any given reaction condition the optimal time for conversion may be quantified.

Following the conversion of the 20 steroid carboxaldehyde to its acetal in the presence of the 3,20 dione steroid, the solvent extraction step is conducted. The theoretical basis of the solvent extraction step is founded upon the fact that the corresponding acetal of the 20 steroid carboxaldehyde differs substantially in solubility in various solvents from that of the 3,20 dione steroid. That is, the 3,20 dione steroid will be quite insoluble in hydrocarbon solvents whereas the acetal will be quite soluble in the same solvent. Convenient hydrocarbon solvents are nonaromatic preferably those alkanes containing 5 or more carbon atoms. A necessary limitation upon the hydrocarbon solvent is that the solvent be, of course, a liquid at the operating temperature and pressure of the solvent extraction. For practical purposes the hydrocarbon solvent may be a pentane, hexane, heptane or mixtures thereof. Included in the foregoing group of hydrocarbon solvents are all the isomers of the foregoing compounds. A most preferred hydrocarbon solvent is normal hexane. Of course, it is recognized that any solvent may be used which allows for substantial separation of the acetal from the 3,20 dione steroid.

It should be understood that the term solvent extraction embraces liquid-liquid extraction or crystallization from the reaction mixture either during or after the acetal formation. It is also noted that suitable solvent systems may be utilized where the 3,20 dione steroid is solubilized and the acetal is relatively insoluble.

The amount of the solvent utilized in the extraction is simply a convenient amount sufficient to separate out substantially all of the acetal without solubilizing more than small amounts of the 3,20 dione steroid. Thus, by determining the solubility of both the acetal and the 3,20 dione steroid separately it is possible to determine the amount of solvent which will accomplish the separation either with one or multiple extraction steps. The temperature range for the solvent extraction is conveniently maintained at from about 35 degrees C. to about =25 degrees C.

The present invention also contemplates the additional step of converting the acetal fraction following the solvent extraction through hydrolysis to regenerate the 20 steroid carboxaldehyde. The regenerated 20 steroid carboxaldehyde may then be separated from the hydrocarbon solvent and recycled for conversion to the 3,20 dione steroid via ozonolysis.

It is also suggested in the present invention that the acetal containing mixture comprising the acetal and the 3,20 dione steroid be neutralized following the acetal formation. This may be done with any convenient Lewis base, such as sodium methylate or caustic. The neutralized mixture of the acetal and the 3,20 dione steroid may be treated to remove the excess solvent at reduced pressure.

Where the alcohol is used as a solvent it is removed as discussed above and the residue containing the acetal and the 3,20 dione steroid is taken up in an aromatic solvent such as toluene, xylene or benzene and washed with water thereby removing inorganic impurities. The aromatic solvent is then removed so as to leave the 3,20 dione steroid and the acetal in approximately the same proportions as in the reaction mixture. That is, the 3,20 dione steroids tend to be quite soluble in an aromatic solvent as is the acetal. Thus, aromatic solvents may be used for washing purposes but not for separation of the acetal from the mixture. The separation of the acetal in the washed system is then accomplished with the hydrocarbon solvent.

Alternatively, the entire reaction is conducted in the hydrocarbon solvent such that the 3,20 steroid is dispersed but not soluble to any extent in the mixture. The washing and neutralization steps may also be conducted in this variation, but not the aromatic solvent treatment to avoid solubilizing the 3,20 dione steroid. This aspect of the invention has the advantage of using a single solvent system throughout the process.

The following exemplifies the present invention:

EXAMPLE I

A mixture containing one kilogram of 3-keto-4-pregnene-20-carboxaldehyde and four kilograms progesterone is solubilized by heating in 50 liters of 1-butanol and followed by cooling to 25 degrees C. Added to the reaction mixture is 10 grams of p-toluenesulfonic acid and 0.5 liter (1 eq) of triethylorthoformate. The reaction mixture is stirred moderately at 22 degrees C. for 1¾ hours.

At the end of this time, a thin layer chromatography test showed no detectable 3-keto-4-pregnene-20-carboxaldehyde. The 20 steroid carboxaldehyde had been substantially converted to the di-normal butyl acetal. The progesterone in the reaction mixture was not affected during the acetal formation.

A sufficient quantity of sodium methylate was added to the reaction mixture to neutralize the p-toluenesulfonic acid rendering the final reaction mixture alkaline. After the neutralization, the excess 1-butanol was removed at reduced pressure. The residue, following solvent removal was taken up in benzene and washed with water to remove any inorganic impurities present. The benzene was then removed and the residue containing the acetal and progesterone was refluxed in the presence of 50 liters of normal hexane.

After about 3 hours the hexane was cooled to about −10 degrees C. The progesterone crystallized in the hexane and the crystals were collected by filtration. The acetal was carried through the filter paper and remained with the hexane filtrate.

Gas chromatagraphy shows that in excess of 90% of the crystalline material is progesterone and less than 1% of the original aldehyde.

The di-normal butyl acetal of the 3-keto-4-pregnene-20-carboxaldehyde may be conveniently regenerated by hydrolysis to give the original 20 steroid carboxaldehyde and butanol. The 3-keto-4-pregnene-20-carboxaldehyde is then recycled as previously discussed.

The foregoing example gives a convenient method for separating progesterone from the corresponding aldehyde with a high degree of purity. Substitutions in the present invention include substituting for the 1- butanol, materials such as 2-butanol, 2-propanol and 1-propanol with substantially similar results.

EXAMPLE II

A mixture containing one kilogram of 3-keto-4-pregnene-20-carboxaldehyde, four kilograms progesterone and 0.5 liter 2-butanol is suspended in 45 liters of normal hexane. Added to the reaction mixture is 10 grams of p-toluenesulfonic acid and 1.0 liter (2 eq) of triethylorthoformate. The reaction mixture is stirred moderately at 22 degrees C. for 4 hours.

At the end of this time, a thin layer chromatography test showed no detectable 3-keto-4-pregnene-20-carboxaldehyde. The 20 steroid carboxaldehyde had been substantially converted to the di-sec butyl acetal.

Any excess alcohol is removed and the progesterone which is insoluble in the hexane is collected by filtration. A yield of progesterone in excess of 83% is obtained with a purity of 99%. The additional step of neutralization and water washing may be conducted in the above example if desired.

What is claimed is:

1. A process for separating 3-keto-4-pregnene-20-carboxaldehyde from a reaction mixture containing progesterone and said 20 steroid carboxaldehyde by the transformation of the aldehyde to the corresponding acetal followed by solvent extraction of the acetal and progesterone into separate fractions.

2. The process of claim 1 wherein the acetal is formed from an alcohol having 3 or more carbon atoms.

3. The process of claim 1 wherein alcohol used to accomplish the acetal formation is employed in a sufficient quantity to function as a solvent during the acetal formation.

4. The process of claim 1 wherein the weight ratio of the 20 steroid carboxaldehyde in the initial reaction mixture to the 3,20 dione steroid is at from about 5:1 to about 1:20.

5. The process of claim 1 wherein the acetal is that corresponding to the 20 steroid carboxaldehyde and a member selected from the group consisting of 1-butanol, 2-butanol, 1-propanol, isobutyl alcohol, and 2-propanol, and mixtures thereof.

6. The process of claim 1 wherein the temperature during the solvent extraction is from about 35 degrees C. to about −25 degrees C.

7. The process of claim 1 comprising the additional step of converting the acetal fraction by hydrolysis to the 20 steroid carboxaldehyde.

8. The process of claim 1 wherein a Lewis acid is employed to promote the acetal formation.

9. The process of claim 8 wherein the reaction mixture contains a Lewis acid selected from the group consisting of p-toluenesulfonic acid, anhydrous hydrochloric acid, trifluoroacetic acid, trichloroacetic acid, oxalic acid and mixtures thereof.

10. The process of claim 1 wherein a desicant is employed to promote the acetal formation.

11. The process of claim 10 wherein the desicant is triethylorthoformate.

12. The process of claim 9 wherein the Lewis acid is p-toluenesulfonic acid.

13. The process of claim 1 wherein the solvent extraction is conducted with a non-aromatic hydrocarbon solvent.

14. The process of claim 13 wherein the hydrocarbon solvent is selected from alkanes containing 5 or more carbon atoms and mixtures thereof.

15. The process of claim 14 wherein the hydrocarbon solvent is selected from the group consisting of pentanes, hexanes, and heptanes and mixtures thereof.

16. The process of claim 15 wherein the hydrocarbon solvent is normal hexane.

17. The process of claim 5 wherein the acetal is that of 1-butanol.

18. The process of claim 1 containing the additional step of neutralizing any acidic component in the acetal containing mixture.

19. The process of claim 18 wherein the neutralization is conducted using sodium methylate.

20. The process of claim 1 containing the additional step of solubilizing the acetal containing mixture in an aromatic solvent and washing with water to remove inorganic impurities.

21. The process of claim 20 wherein the aromatic solvent is benzene.

22. The 22-acetal of the corresponding 3-keto-4-pregnene-20-carboxaldehyde.

23. The 22-acetal of claim 22 wherein the acetal has at least 3 carbon atoms in the alcohol portion of the acetal structure.

24. The compound of claim 25 wherein the acetal is the di-n-butylacetal of 3-keto-4-pregnene-20-carboxaldehyde.

25. The compound of claim 23 wherein the acetal is the di-sec-butylacetal of 3-keto-4-pregnene-20-carboxaldehyde.

UNITED STATES PATENT AND TRADEMARK OFFICE
CERTIFICATE OF CORRECTION

PATENT NO. : 4,201,716
DATED : 05/06/80
INVENTOR(S) : LeRoy O. Krbechek

It is certified that error appears in the above-identified patent and that said Letters Patent are hereby corrected as shown below:

Cover page, Abstract; the reference to "$C_{21}$" should read, -- $C_{22}$ -- as in the title.

Column 1, line 16; "chlorenaldehyde" should read, -- cholenaldehyde --.

Column 3, Structure III; the structure should have lines there indicating carbon bonds within the ring so that there are 4 rings instead of two.

Column 3, structure V; both the references below it should read -- 22 -- acetyl or butylacetal, not "21".

Column 4, line 12; "scavange" should read -- scavenge --.

Column 5, line 55; "=25" should read -- -25 --.

Signed and Sealed this

Twenty-third Day of July 1985

[SEAL]

Attest:

DONALD J. QUIGG

Attesting Officer   Acting Commissioner of Patents and Trademarks